United States Patent [19]

Travanty et al.

[11] Patent Number: 4,987,583
[45] Date of Patent: Jan. 22, 1991

[54] AUTOMATIC BACKOUT CONTROL FOR A MOTORIZED POSITIONING X-RAY APPARATUS

[75] Inventors: Frank C. Travanty, Waukesha; Philip M. Allen, Oconomowoc; Vinod K. Chopra, Brookfield, all of Wis.

[73] Assignee: General Electric Company, Milwaukee, Wis.

[21] Appl. No.: 343,462

[22] Filed: Apr. 25, 1989

[51] Int. Cl.$^5$ .............................................. H05G 1/08
[52] U.S. Cl. ........................................ 378/91; 378/95; 378/197
[58] Field of Search ................... 378/4, 15, 20, 91, 95, 378/205, 195-198

[56] References Cited

U.S. PATENT DOCUMENTS

| | | | |
|---|---|---|---|
| 2,749,445 | 6/1956 | Stava et al. | 378/91 |
| 3,783,251 | 1/1974 | Pavkovich | 378/196 |
| 4,107,590 | 8/1978 | Pury et al. | 318/628 |
| 4,358,856 | 11/1982 | Stivender et al. | 378/167 |
| 4,392,096 | 7/1983 | Grajewski et al. | 318/625 |
| 4,448,200 | 5/1984 | Brooks et al. | 378/20 |
| 4,578,757 | 3/1986 | Stark | 250/363.02 |
| 4,807,273 | 2/1989 | Haendle | 378/197 |

Primary Examiner—Edward P. Westin
Assistant Examiner—Kim-Kwok Chu
Attorney, Agent, or Firm—Quarles & Brady

[57] ABSTRACT

An X-ray apparatus has motors for moving its components in different directions. Sensors are provided to detect a collision between a motor driven component and an object, such as a patient being examined. In response to a collision being detected, a normal motor power supply is disconnected from the motor and another power supply is connected to the motor to move the component in the reverse direction. A safeguard is incorporated to insure that both power supplies cannot be coupled to the motor at the same time. For components which can strike a patient when moving in either of two directions, different collision sensors are provided for each direction. For this configuration, a mechanism also is provided to inhibit the connection of the other power supply when collisions are simultaneously detected each direction of component movement.

16 Claims, 2 Drawing Sheets

AUTOMATIC BACKOUT CONTROL FOR A MOTORIZED POSITIONING X-RAY APPARATUS

BACKGROUND OF THE INVENTION

The present invention relates to automatic control systems for motorized positioners in X-ray systems; and particularly to such control systems which detect and respond to collisions between the X-ray equipment and an object.

In relatively large X-ray systems, such as shown in U.S. Pat. No. 4,358,856, the X-ray source and film holder are mounted on a gantry which allows the components to be positioned at different angles with respect to the patient. For example, during angiographic procedures, X-ray exposures are taken of the patient at a number of angles from the frontal projection through a plurality of oblique projections to a lateral projection, and through a plurality of head to foot angles in concert with the frontal and oblique projections. In order to position the gantry at each of the angles at which an exposure is to be taken, a series of motors move the gantry components with respect to the patient. The electrical drive circuitry for each motor is controlled by a set of push buttons operated by the X-ray technician.

Because the X-ray equipment is moving about a relatively immobile patient, a safeguard mechanism must be provided in the event of a collision between the moving equipment and the patient. In the past, sensors were mounted on various components of the gantry which were likely to come into contact with the patient or the X-ray technician, during the operation of the equipment. In response to the sensors detecting a collision between the equipment and another object, the drive circuitry for the gantry motors was disabled until manually reset.

Although this safeguard technique prevented serious injury to the patient and to the X-ray technician, the individual or object with which the equipment collided might be wedged between different components of the X-ray system. Since the collision could occur due to a malfunction in the motor drive circuitry, the motor could not be used to move the equipment in the opposite direction to extricate the trapped individual. Furthermore, because of the motor gearing and the heavy weight of the gantry components, movement of the components by hand to free the individual was often extremely difficult.

SUMMARY OF THE INVENTION

Each motor for positioning components in an X-ray system has a conventional motor drive circuit for positioning the associated X-ray component utilizing that motor under normal operating conditions. In the event of a collision between an X-ray system component and another object, such as a patient or X-ray technician, the normal motor drive circuit is disabled and a separate backout drive circuit is coupled to the motor. This backout drive circuit responds to the detection of a collision by applying electricity to the motor associated with positioning the component with which the collision occurred. This application of electricity reverses the direction of the motor, backing the associated component out of contact with the object. Once the contact with the object is no longer being detected, the collision detection circuitry restores the control of the associated motor to the normal motor drive circuit allowing the X-ray technician to move the X-ray equipment via a set of manual switches.

An object of the present invention is to provide a mechanism for responding to collisions between motor driven components of an X-ray system and a foreign object using a separate motor control circuit from that which drove the component into the collision. In this manner, a motorized reversal of the equipment movement is accomplished without relying on the normal motor drive circuit which produced the collision.

Another object of the present invention is to provide a mechanism for disabling the normal motor drive circuit and enabling the back out motor drive circuit upon a collision being detected.

A further object of the present invention is to provide a safeguard mechanism so that both the normal and collision back out drive circuits cannot be coupled to the motor simultaneously.

Yet another object is to provide a time delay before either of the drive circuits is coupled to the motor to allow the back emf in the motor to decay. However, this delay circuit must not affect the rapid disconnect of the drive circuits from the motor.

DETAILED DESCRIPTION OF THE INVENTION

Figure 1:
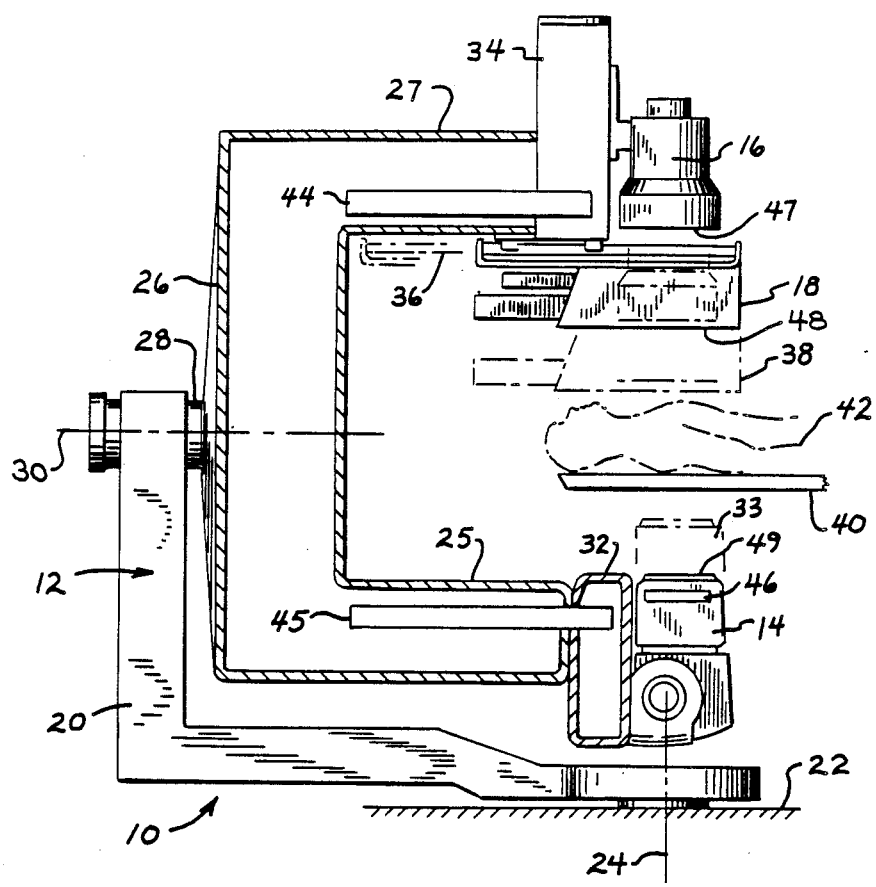
FIG. 1 is a side view of an X-ray system incorporating the present motor control circuit.

With initial reference to FIG. 1, an X-ray system, generally designated as 10, includes a gantry 12 on which are mounted an X-ray source 14, an image intensifier/video camera assembly 16, and a rapid film changer 18. This type of X-ray system is described in U.S. Pat. No. 4,358,856 which description is incorporated by reference herein.

The gantry 12 includes an L-shaped arm 20 which is pivotally mounted at one end to the floor 22 of the room enclosing the X-ray system. The pivotal mounting enables the L-shaped arm 20 (and the entire gantry) to be rotated about a vertical axis 24. The gantry 12 also includes a U-shaped arm 26 mounted at the other end of the L-shaped arm 20. The two arms 20 and 26 are connected by a motor 28, which when energized, rotates the U-shaped arm about a horizontal axis 30 in either the clockwise or counterclockwise direction. The motor is controlled by pushbutton switches on an X-ray technician's control panel (not shown).

The X-ray source 14 is mounted at the remote end of a first projection 25 of the U-shaped arm 26 by a source carriage 32. The X-ray source 14 incorporates a conventional X-ray tube and associated components for emitting an X-ray beam across the opening of the U-shaped arm 26 toward the remote end of the arm's second projection 27. A motorized assembly within the U-shaped arm 26 causes the source carriage 32 and the X-ray source 14 mounted thereon to move within the plane of the U-shaped arm (up and down in the orientation illustrated in FIG. 1). For example, another position of the X-ray source 14 is represented by phantom lines 33.

A head carriage 34 is mounted at the remote end of the U-shaped arm's second projection 27 and supports the image intensifier/video camera assembly 16 and the rapid film changer 18. When the rapid film changer 18 is in the position illustrated in FIG. 1, the X-rays from the source 14 expose the film contained within the changer. Alternatively, the rapid film changer 18 may be slid out of the X-ray beam path into a position illustrated by phantom lines 36. In this alternative position, the X-ray beam from source 14 strikes the image intensifier/video camera assembly 16 which produces a video signal representing the X-ray image. The U-shaped arm 26 includes a motorized mechanism for moving the head carriage 34 within the plane of the U-shaped arm (up and down in the orientation illustrated in FIG. 1). This movement enables the rapid film changer 18 to be positioned at different locations, such as the ones illustrated by the solid lines of the figure and by phantom lines 38. In addition to the image intensifier/video camera assembly 16 moving with the movement of the head carriage 34, a separate motorized mechanism is provided to move the image intensifier/video camera assembly 16 with respect to the head carriage 34.

An X-ray transmissive table 40 extends into the central opening of the U-shaped arm 26 to support a patient 42 being examined. The patient 42 lies on the horizontal axis 30 of the gantry 12 permitting the U-shaped arm 26 and the components mounted thereon to revolve around the patient, enabling X-ray exposures to be taken at various angles with respect to the patient.

As can be visualized, the gantry arms 20 and 26, the X-ray source 14, the image intensifier/video camera assembly 16, and the rapid film changer 18 all can be moved with respect to the position of the patient 42. Under ordinary circumstances, this movement is relatively slow and can be easily controlled by the X-ray technician. However, should a failure occur in the circuits supplying electricity to the gantry motors, it is possible for one of the components to strike the patient accidentally. Furthermore, the X-ray technician typically stands relatively close to the equipment while positioning the gantry with respect to the patient. For example, the X-ray technician could be straddling the L-shaped arm 20 as the U-shaped arm 26 is being rotated. Therefore, it is conceivable that one of the X-ray system components could strike the X-ray technician and possibly wedge the individual between various ones of the system components.

In order to detect such collisions, sensors are mounted on components of the X-ray system 10 at positions which are likely to contact the patient. For example, a pressure sensor 44 is placed on one side of the second projection 27 of the U-shaped arm 26 and a second pressure sensor 45 is placed in a similar position on the first projection 25. A pressure sensor 46 is mounted on the side of the X-ray source 14 to detect a collision between that component and another object. Other sensors are mounted in corresponding positions on the other sides of the U-shaped arm 26 and the X-ray source 14 which are hidden from view in the figure. Similar sensors 47, 8, and 49 are mounted on the surfaces of the image intensifier/video camera assembly 16, the rapid film changer 18, and the X-ray source 14, respectively, which face the patient 42. All of the pressure sensors 44–49 respond to contact with another object by closing an electrical switch, thereby providing an electrical signal which indicates a collision.

Figure 2:
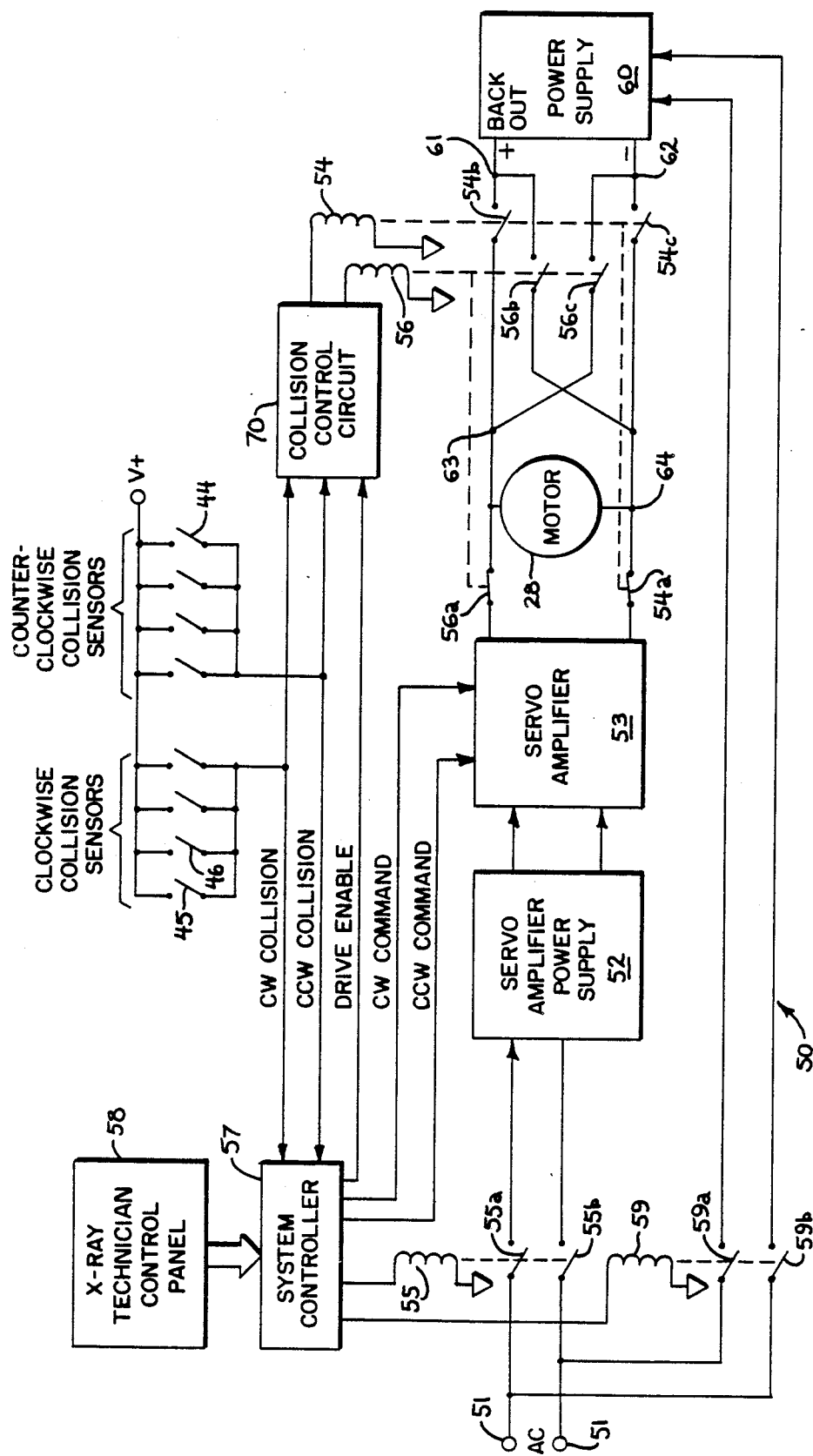
FIG. 2 is a schematic block diagram of a motor control circuit incorporating the present invention.

FIG. 2 illustrates a control circuit 50 for the motor 28 which moves the U-shaped arm 26. The motor is controlled by a pair of pushbutton switches on the X-ray technician control panel 58, one switch for clockwise motion and the other for clockwise movement. When one of these pushbuttons is pressed to move the U-shaped arm 26, a conventional system controller 57 responds by energizing relay coil 55 to close switch contacts 55a and 55b. Alternating current for the control circuit is provided to terminals 51 which are coupled to a servo amplifier power supply 52 by the relay switch contacts 55a and 55b. In addition the activation of the pushbutton also causes the system controller to generate an active DRIVE ENABLE signal until the pushbutton is released. This portion of the system controller 57 uses only passive devices, such that a failure in any device will cause the DRIVE ENABLE signal either to go inactive or to allow the technician's push button to drop the DRIVE ENABLE signal.

Typically direct current motors are employed in the X-ray system in order to provide easily reversible motion. The servo amplifier power supply 52 rectifies the alternating current to provide power for the motor 28. The rectified output from the servo amplifier power supply 52 is applied to the input of a conventional servo amplifier 53. The output of the servo amplifier 53 is coupled by two normally closed relay contacts 54a and 56a to the motor 28 being driven. The servo amplifier 53 receives two control signals, designated CW COMMAND and CCW COMMAND which are generated by the X-ray system controller 57 in response to the activation of pushbutton switches on the X-ray technician control panel 58, as in previous motorized systems. An active CW COMMAND signal enables the servo amplifier to produce a direct current output having a polarity which causes the motor 28 to rotate the U-shaped arm 26 in a clockwise direction; whereas the CCW COMMAND signal causes the servo amplifier to produce a direct current of the opposite polarity resulting in the motor 28 rotating the U-shaped arm in the counterclockwise direction.

The alternating current input terminals 51 also are coupled, via relay switch contacts 59a and 59b, to a backout power supply 60. The relay switch contacts 59a and 59b are activated by a relay coil 59 which also is energized by the system controller 57 in response to pressing a motor control switch on the X-ray technician control panel 58. The backout power supply receives power from the AC terminals 51 whenever the motor 28 is active, but is interlocked from driving the motor unless a collision occurs and a proper control transition is effected. The X-ray technician always is able to stop the motion regardless of whether the motor 28 is receiving power from the servo amplifier 53 or from the backout power supply 60. The release of the control panel pushbutton de-energizes both relay coils 55 and 59.

Application of power to the backout power supply 60 produces a dc voltage across positive output terminal 61 and negative output terminal 62. The power supply output terminals 61 and 62 are coupled to terminals 63 and 64 of the motor 28 by a reversing contactor mechanism consisting of relay switch contacts 54b and 54c and relay switch contacts 56b and 56c. Specifically, the positive output terminal 61 is coupled to terminal 63 of the motor by a normally open relay contact 54b and to motor terminal 64 by a normally open relay contact 56b. The negative terminal 62 of the backout power supply 60 is connected to terminal 63 of the motor by a normally opened relay contact 56c and to motor terminal 64 by a normally opened relay contact 54c.

As indicated by dashed lines in FIG. 2, relay switch contacts 54a, 54b, and 54c are actuated by relay coil 54; and relay switch contacts 56a, 56b, and 56c are actuated in common by another relay coil 56. Relay coils 54 and 56 are mutually exclusive and are interlocked from being energized simultaneously, as will be described.

Selected pressure sensors, such as sensors 45 and 46, which are likely to detect a collision when the U-shaped arm 26 is moving clockwise, are connected in parallel to generate a signal designated CW COLLISION. Similarly, other pressure sensors, such as sensor 44, which are likely to detect a collision when the U-shaped arm is traveling counterclockwise, are connected in parallel to generate a signal designated CCW COLLISION. The CW and CCW COLLISION signals are connected to the system controller 57. In response to either the CW or CCW COLLISION signals, the system controller 57 de-energizes relay coil 55, thereby disconnecting the power to the servo amplifier 53 and the motor 28.

Figure 3:
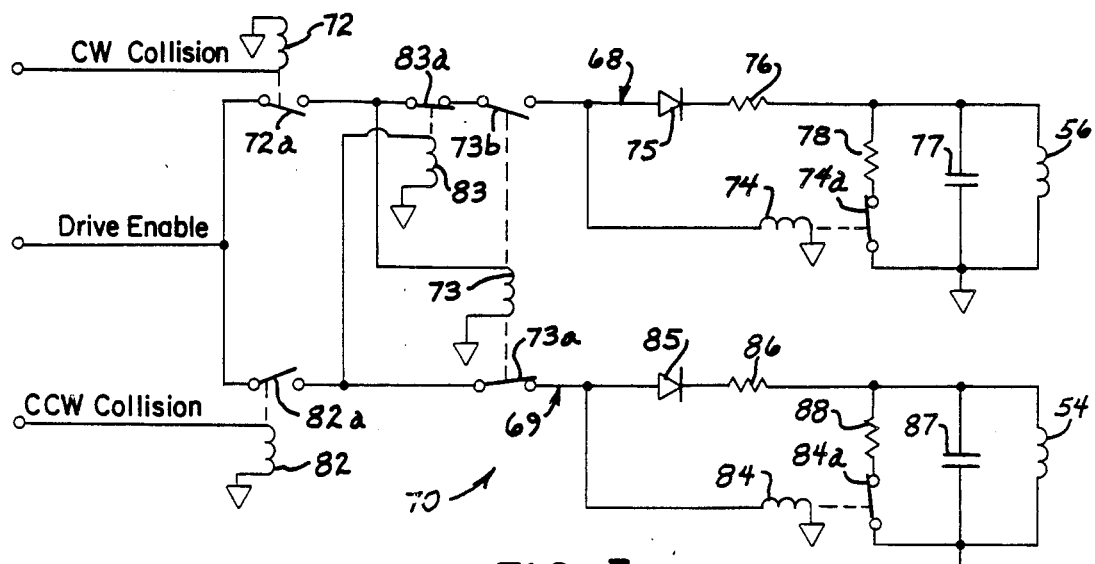
FIG. 3 is a collision safeguard control circuit for operating the switches in the control system of FIG. 2.

The CW and CCW COLLISION signals also are coupled to the collision control circuit 70, illustrated in detail in FIG. 3. The collision control circuit 70 consists of two virtually identical circuit branches 68 and 69. The first branch 68 is activated by a collision when the gantry is traveling in the clockwise direction, and the second branch 69 is activated a collision occurs while the gantry is traveling in the counterclockwise direction.

A relay switch contact 72a in the first branch 68 is closed by an active CW COLLISION signal applied to the coil 72 of a clockwise collision relay. The closure of switch contact 72a sends a current from the active DRIVE ENABLE signal through relay coil 73, which opens normally closed switch 73a in the second branch 69 and then closes normally open switch 73b in the first branch 68. This opening of the normally closed switch 73a disables the second branch of the collision control circuit 70. The activation of relay coil 73 opens switch 73a before closing switch 73b thereby insuring that only one branch of the collision control circuit is active at any one time.

The current through switch contacts 72a passes through closed switches 83a and 73b to relay coil 74, causing normally closed switch 74a to disconnect resistor 78 from the circuit. The current from the closure of switch contacts 72a also flows through diode 75 and resistor 76 to the parallel connection of motor control relay 56 and capacitor 77 and to ground. The resistance of elements 76 and 56 and the capacitance of capacitor 77 form an RC network having a time constant which provides a small delay before enough current flows through the motor control relay coil 56 to activate its contacts 56a–56c. As noted above, the CW COLLISION signal caused the system controller 57 to disconnect the power to the motor 28 from the servo amplifier 53. This delay insures that any back electromotive force developed in the motor 28 during deceleration will have decayed to a negligible level before current is reapplied to the motor to reverse its direction.

At the end of the time delay, the current flowing through the motor control relay coil 56 activates its switch contacts 56a–56c shown on FIG. 2. This activation opens the set of contacts 56a to disconnect the servo amplifier 53 from the motor 28 before the pair of contacts 56b and 56c are closed to couple the output from the backout power supply 60 to motor 28. The closure of contacts 56b and 56c applies a dc polarity to the motor 28 which causes the motor to drive the U-shaped arm 26 in a counterclockwise direction, opposite to the clockwise direction at which the U-shaped arm was traveling at the time of the collision. This action automatically backs the U-shaped arm away from the object with which it collided. The movement of the U-shaped arm 26 continues until the pressure sensor which initiated the movement reversal no longer detects contact with the object. The resultant reverse movement of the U-shaped arm 26 in response to the sensed collision is sufficient to permit the object which was struck to be removed from the point of collision.

Once the switch of the pressure sensor opens, the CW COLLISION signal goes inactive opening relay switch contact 72a. This action de-energizes relay coils 73, 74, and 56 of the collision control circuit 70. When relay coil 74 is de-energized, switch 74a closes connecting fixed resistor 78 in parallel with the relay coil 56. This resistor 78 provides a shunt path for the charge accumulated on capacitor 77 causing a rapid de-energization of relay coil 56. As a result, the contacts 56a–56c, controlled by relay coil 56, rapidly change states. Specifically, switch contacts 56b and 56c open and then contact 56a returns to its normally closed state. This action disconnects the backout power supply 60 from the motor 28 and connects the servo amplifier once again to the motor 28. The cutoff of current through relay coil 73 closes switch 73a, rendering the second branch 69 of the collision control circuit operative.

Even though the servo amplifier 53 is again connected to the motor 28, the system controller 57 has not energized relay coil 55 and the AC power is not applied to the servo amplifier power supply 52. Therefore, the motor is not being powered by the servo amplifier 53. This action prevents the motor control circuit 50 from repeatedly driving the arm against an object and then backing away. As a safeguard, before the system controller 57 again energizes relay coil 55, the X-ray technician must release and then press again the pushbutton switch on control panel 58 to resume normal motor control.

The second branch 69 of the collision control circuit 70 in addition to including switch 73a has a similar set of components 82–88 to those described with respect to the first branch 68. However, relay coil 82 responds to the CCW COLLISION signal produced by a collision with an object while the U-shaped arm 26 is moving counterclockwise. Briefly, when such a collision is detected and switch 82a closes, relay coil 83 is energized opening the normally closed switch 83a in the first branch 68 of the collision control circuit 70, disabling that branch's circuitry. The current through switch 82a also energizes relay coil 54 in a manner similar to the way in which the relay coil 56 in the other branch was activated. However, relay coil 54 opens the normally closed switch contact 54a disabling servo amplifier 53 from applying electricity to the motor 28. The relay coil 54 also closes the pair of contacts 54b and 54c applying the opposite dc polarity from the power supply 60 to the motor 28 as that applied by the contacts 56b and 56c. As a consequence, the motor 28 drives the U-shaped arm 26 in a clockwise direction, or opposite to the direction at which it was traveling when the collision occurred.

In the unlikely event that the pressure sensors 44–49 simultaneously indicate a collision in both the clockwise and the counterclockwise directions, both branches 68 and 69 of the collision control circuit 70 will be disabled. In this case, both the clockwise collision relay switch contact 72a and the counterclockwise collision relay switch contact 82a are closed, thereby applying current to corresponding relay coils 73 and 83. As a result, switches 83a and 73a are opened rendering both branches 68 and 69 inoperative insofar as controlling the motor. This operation provides an additional safeguard mechanism, since when simultaneous clockwise and counterclockwise collisions are sensed, the control circuit 70 is unable to determine in which direction the U-shaped arm 26 may be moved safely. Therefore, in the event of simultaneous collisions in both directions of movement, the collision control circuit 70 is rendered inoperative until one of the collisions is no longer sensed.

Although the previous description of the motor control circuitry has been described in terms of the U-shaped arm 26, similar control circuits are used with respect to the motor which moves the X-ray source 14, the motor for the movement of the head carriage 34, and the motor coupled to the image intensifier/video camera assembly 16. Although a similar bidirectional collision control circuit, as is shown in FIGS. 2 and 3, can be provided for these motors, the primary concern is the collision of the X-ray system components with the patient 42. Therefore, sensors 47, 48, and 49 are located on these components in positions facing the patient. Furthermore, since such collisions will occur only when these components are traveling in a direction toward the patient, the movement in response to a collision will always be in the same direction away from the patient As a result, only a single branch of the collision control circuit in FIG. 3 is necessary with respect to these other three motors and only one pair of contacts 54b-54c or 56b-56c are required to couple a backout power supply to the motor, depending upon the direction of the motor required for that backout movement.

We claim:

1. In an X-ray apparatus having a structural member driven by a motor, a motor control circuit comprising:
    a first power supply for applying electricity to said motor, in response to command signals from an operator, to move the structural member in one of two directions;
    means for detecting contact between the structural member and an object;
    a second power supply for the motor;
    means, responsive to said means for detecting, for disabling said first power supply from applying electricity to said motor; and
    means, responsive to said means for detecting, for connecting said second power supply to the motor to cause the motor to move the structural member away from contact with the object.

2. The motor control circuit as recited in claim 1 wherein said means for connecting said second power supply to the motor is inhibited from making the connection until the first power supply has been disabled from applying electricity to the motor.

3. The motor control circuit as recited in claim 2 wherein means for connecting said second power supply to the motor is inhibited from making the connection for a predefined interval after the first power supply has been disabled from applying electricity to said motor.

4. The motor control circuit as recited in claim 1 wherein said means for connecting further responds to the means for detecting such that, when the structural member moves away from contact with the object, the second power supply is disconnected from the motor.

5. The motor control circuit as recited in claim 4 further comprising means for reenabling the first power supply after the structural member moves away from contact with the object.

6. The motor control circuit as recited in claim 5 wherein said means for reconnecting the first power supply to the motor in inhibited from doing so until after the second power supply has been disconnected from the motor.

7. A control circuit for an electric motor comprising:
    a first source of power for driving the motor to move a device coupled to the motor in either a first or a second direction;
    a second source of power for the motor;
    first means for detecting contact between the device and an object when the motor is moving the device in the second direction;
    first means for disabling said first source of power from driving the motor when said first means for detecting detects the contact; and
    first means for connecting said second source of power to said motor to drive the motor and move the device in the first direction when said first means for detecting detects the contact.

8. The control circuit for an electric motor as recited in claim 7 wherein said first means for connecting said second source of power to the motor is inhibited from making the connection until the first source of power has been disabled from driving the motor.

9. The control circuit for an electric motor as recited in claim 8 wherein said first means for connecting said second source of power to the motor is inhibited from making the connection for a given interval after the first source of power has been disabled from driving the motor.

10. The control circuit for an electric motor as recited in claim 7 further comprising:
    second means for detecting contact between a device coupled to the motor and an object when the motor is being driven in the first direction;
    second means for disabling said first source of power from driving the motor when said second means for detecting detects the contact; and
    second means for connecting said second source of power to said motor to drive the motor in the second direction when said second means for detecting detects the contact.

11. The control circuit for an electric motor as recited in claim 10 wherein said first and second means for connecting said second source of power to the motor are inhibited from making the respective connections until the first source of power has been disabled from driving the motor.

12. The motor control circuit for an electric motor as recited in claim 11 wherein said first and second means for connecting said second source of power to the motor are inhibited from making the respective connections for a given interval after the first source of power has been disabled from driving the motor.

13. The control circuit for an electric motor as recited in claim 11 further comprising means for preventing the first and second means for connecting from simultaneously connecting said second source of power to the motor.

14. A control circuit for a direct current motor, which produces movement of a component of a medical apparatus, the motor having first and second terminals, said control circuit comprising:

means for applying one of two polarities of a dc voltage to the motor terminals in response to a control signal, thereby causing the motor to drive the component in either a first or a second direction;

a source of dc voltage having a positive and a negative terminal;

first means for sensing contact between the component of the medical apparatus and an object when the component is being driven in the first direction;

second means for sensing contact between the component of the medical apparatus and an object when the component is being driven in the second direction;

means for disabling said means for applying in response to the first and second means sensing contact;

first switch means, responsive to the first means for sensing contact, for connecting the positive terminal of said source of dc voltage to the first terminal of said motor, and for connecting the negative terminal of said source of dc voltage to the second terminal of said motor; and second switch means, responsive to the second means for sensing contact, for connecting the negative terminal of said source of dc voltage to the first terminal of said motor, and for connecting the positive terminal of said source of dc voltage to the second terminal of said motor.

15. The motor control circuit as recited in claim 14 further comprising means for preventing said first and second switch means from simultaneously connecting said source of a dc voltage to the motor.

16. The motor control circuit as recited in claim 14 further comprising means for preventing said first and second switch means from connecting said source of a dc voltage to the motor until said means for applying has been disabled.

* * * * *